United States Patent
Maxim

[11] Patent Number: 5,887,437
[45] Date of Patent: Mar. 30, 1999

[54] SELF-ADHERING COLD PACK

[75] Inventor: Rosemary S. Maxim, Avon, Conn.

[73] Assignee: Beekley Corporation, Bristol, Conn.

[21] Appl. No.: 940,788

[22] Filed: Sep. 30, 1997

[51] Int. Cl.[6] ............................................. F25D 5/02
[52] U.S. Cl. ................................ 62/4; 62/530; 224/901; 607/112
[58] Field of Search ........................... 62/530, 4; 607/112; 248/205.3, 683; 224/901

[56] References Cited

U.S. PATENT DOCUMENTS

| | | | |
|---|---|---|---|
| 3,630,195 | 12/1971 | Santomieri | 248/205.3 |
| 4,122,857 | 10/1978 | Haerr | 248/205.3 |
| 4,310,137 | 1/1982 | Frye | 248/205.3 |
| 4,347,848 | 9/1982 | Hubbard et al. | 128/402 |
| 4,413,624 | 11/1983 | Snow | 128/399 |
| 4,517,972 | 5/1985 | Finch, Jr. | 128/156 |
| 4,523,353 | 6/1985 | Hubbard et al. | 24/30.5 R |
| 4,585,003 | 4/1986 | Meistreil | 128/402 |
| 4,834,802 | 5/1989 | Prier | 607/112 |
| 5,052,387 | 10/1991 | Natali | 128/402 |
| 5,062,425 | 11/1991 | Tucker | 128/401 |
| 5,109,841 | 5/1992 | Hubbard et al. | 128/380 |
| 5,167,655 | 12/1992 | McCoy | 604/396 |
| 5,184,613 | 2/1993 | Mintz | 128/402 |
| 5,277,180 | 1/1994 | Angelillo et al. | 607/114 |
| 5,300,103 | 4/1994 | Stempel | 607/112 |
| 5,336,255 | 8/1994 | Kanare et al. | 607/112 |
| 5,431,622 | 7/1995 | Pyrozyk et al. | 602/2 |
| 5,466,251 | 11/1995 | Brunson et al. | 607/112 |
| 5,476,491 | 12/1995 | Mayn | 607/111 |
| 5,514,170 | 5/1996 | Mauch | 62/530 |
| 5,674,270 | 10/1997 | Viltro et al. | 607/112 |
| 5,677,512 | 10/1997 | Reiker | 248/205.3 |
| 5,735,889 | 4/1998 | Burkett et al. | 607/112 |
| 5,766,235 | 6/1998 | Kostopoulos | 62/530 |

*Primary Examiner*—William E. Tapolcai
*Attorney, Agent, or Firm*—Alix, Yale & Ristas, LLP

[57] ABSTRACT

A self-adhering cold pack has an envelope defining a sealed cold pack volume. A cooling agent is positioned in the cold pack volume. A bandage sheet is fixed to the envelope by a bandage adhesive. The bandage sheet defines mounting tabs linearly extending from the envelope outer perimeter. The mounting tabs support a bandage adhesive for temporary adhesion of the cold pack to the skin surface of a patient.

20 Claims, 4 Drawing Sheets

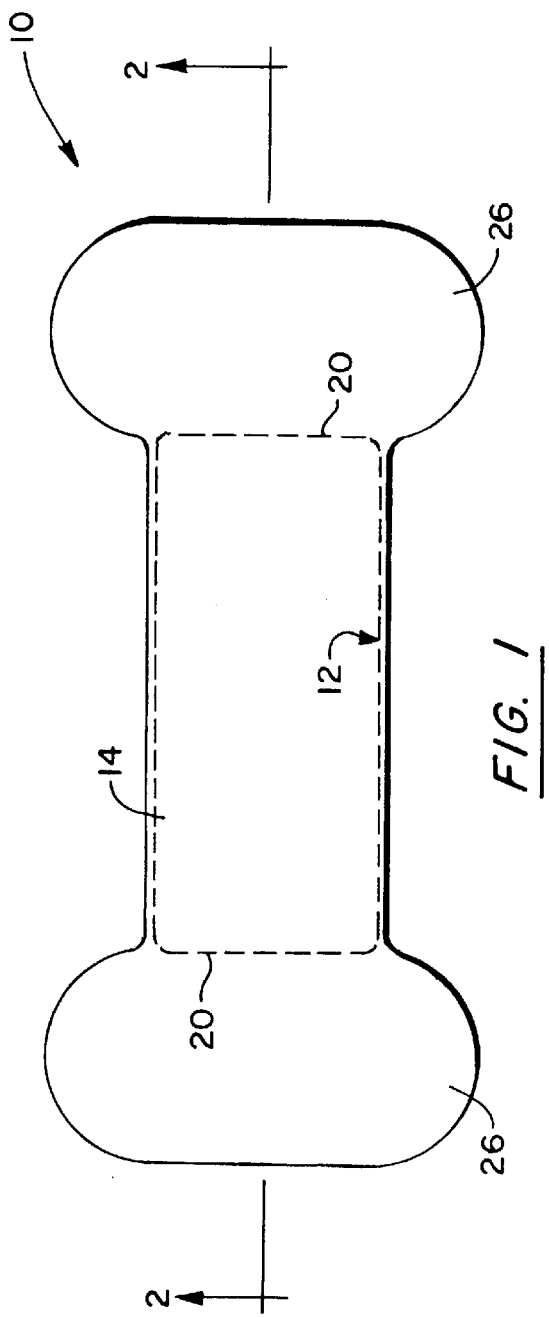
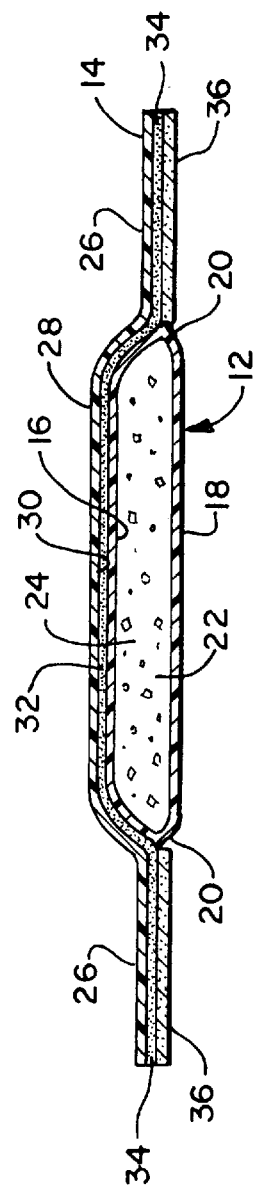

SELF-ADHERING COLD PACK

FIELD OF THE INVENTION

This invention relates to the field of medical devices. More particularly, this invention relates to the field of cold packs for application to a trauma site on a patient.

BACKGROUND OF THE INVENTION

It is well-known to apply cold packs to the skin surface of a patient that has undergone trauma. The cold pack can reduce pain and prevent or reduce swelling. Conventionally, the cold pack, cooled by ice or activated chemicals, is applied to the site of the trauma over bandaging. Cold packs are typically applied at the site of a trauma such as a contusion or sprain. Cold packs are further applied in the area of a laceration that will soon undergo, or have undergone, suturing. A cold pack can be applied to a laceration to act as an anesthetic by numbing the area until a surgeon or physician can suture the wound.

The cold pack is usually held in place by the patient receiving treatment. The requirement to hold the cold pack in position restricts the mobility of the patient and can in some circumstances be uncomfortable. Stretch wraps, tapes or other support materials have been improvised to support cold packs in location on the patient. Typically, these forms of improvised support materials are only appropriate for the limbs or head where the support material can encircle the patient to maintain the cold pack in position. Use of the cold pack in other portions of the body typically again requires the cold pack to be hand held into position. Furthermore in certain types of surgery, particularly nasal or nose surgery, cold packs are required to be applied to the area of trauma for the first 24 to 48 hours. This extended treatment with a cold pack further increases the inconvenience of holding by hand the cold pack on the patient.

Prior designs have attempted to overcome these difficulties with supports having a pouch to receive a cold pack and an encircling portion to surround the limb or head of the patient. These cold pack supports are still inappropriate for some portions of the body.

SUMMARY OF THE INVENTION

Briefly stated, the invention is directed to a self-adhering cold pack. The cold pack in accordance with the invention has an envelope containing a cooling agent. The cooling agent can be a material, such as water, that can be readily frozen in a conventional freezer. The cooling agent can be alternatively separate reactive components, that when combined, undergo an endothermic reaction to provide a cooling effect. Typical reactive components for such endothermic reactions include water and sodium nitrate, and water and ammonium nitrate.

The envelope of the cold pack is formed of a liquid impermeable material and defines a closed or sealed internal cold pack volume. Positioned within the cold pack volume is the cooling agent. A sheet of flexible bandage material is positioned in contact with the envelope and extends beyond the outer perimeter of the envelope to define mounting tabs. The sheet is mounted to the envelope by a mounting adhesive positioned therebetween. A hypo-allergenic bandage adhesive further covers the mounting tabs for holding the cold pack to the patient. A peel-away base sheet preferably covers the bandage adhesive on each mounting tab to maintain the bandage adhesive in good operable condition during transport and storage of the self-adhering cold pack.

A layer of insulation material can also be provided between the bandage sheet and the envelope to extend the cooling effect of the cooling agent.

In a further embodiment, the envelope has a readily rupturable divider wall between separate internal compartments or chambers. Each chamber contains a reactive component that when combined have an endothermic reaction. Therefore, before application of the cold pack to the patient, the envelope is squeezed or struck to rupture the divider wall, thereby allowing the reactive components to combine and undergo the endothermic reaction that provides self-cooling to the self-adhering cold pack. The self-cooling self-adhering cold pack has particular utility in circumstances where the facilities for freezing a cooling agent are unavailable. These include camping, first-aid boxes and at many athletic events.

In an alternate embodiment of the invention, the envelope defines a plurality of adjacent cells or chambers, each containing cooling agent. The individual cells together define a readily flexible envelope for positioning over contoured portions of the patient, in particular, the nose area. The cold pack can be readily configured around the bridge of the nose and under the eyes. The cold pack is maintained in position by the mounting tabs to therefore allow hands free application of the self-adhering cold pack on the nose of a patient with minimal interruption to the movement of the patient.

An object of the invention is to provide a cold pack for application to an area of a patient that has undergone trauma.

A further object of the invention is to provide a cold pack that is self-adhering to a patient.

Another object of the invention is to provide a cold pack that is manufacturable at a reduced cost, and therefore, preferably disposable.

These and other objects of the invention will become apparent from review of the specification and drawings.

BRIEF DESCRIPTION OF THE DRAWINGS

FIG. 1 is a top view of a self-adhering cold pack of the invention;

FIG. 2 is a cross-sectional view of the cold pack of FIG. 1 taken along the line 2—2;

DESCRIPTION OF THE PREFERRED EMBODIMENT

Figure 3:
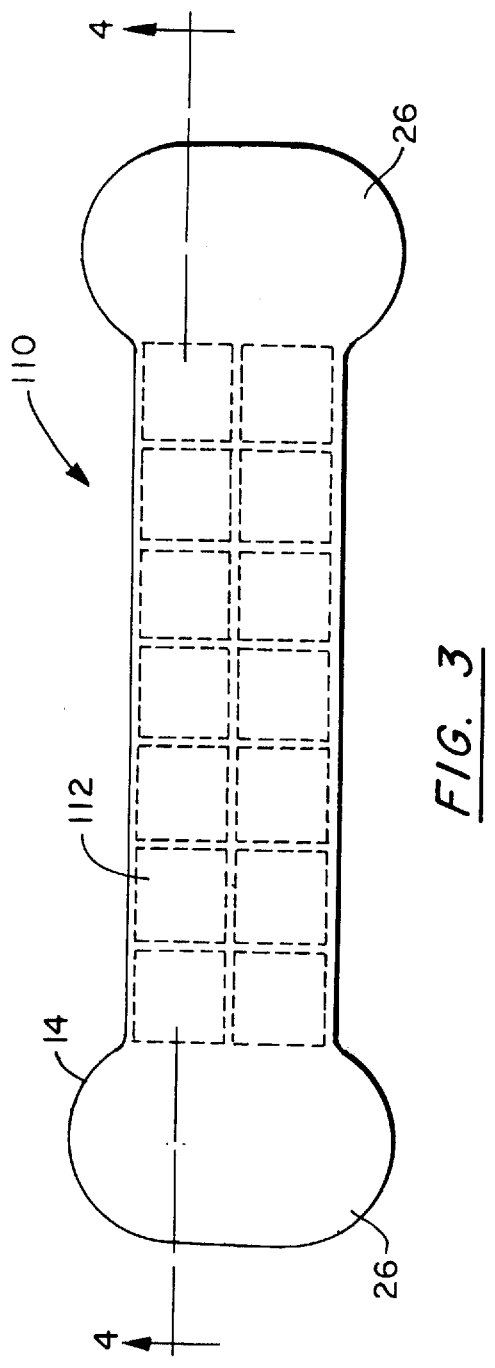
FIG. 3 is a top view, partially in phantom, of an alternate embodiment of the self-adhering cold pack of the invention.

With reference to FIGS. 1 and 2, and wherein like numerical identifiers represent like components throughout the figures, the self-adhering cold pack 10 of the invention has a cold pack envelope 12 and a flexible bandage sheet 14.

The envelope 12 is preferably formed of an upper envelope layer 16 and a lower envelope layer 18, each envelope layer 16, 18 formed of a flexible liquid impermeable material such as plastic. The outer edges of the upper and lower envelope layers 16, 18 are sealed together to form an envelope outer perimeter 20. The upper and lower envelope layers 16, 18 further together define an interior sealed cold pack volume 22.

A cooling agent 24 is positioned within the cold pack volume 22. The cooling agent 24 is preferably a material readily cooled or frozen in a conventional refrigerator. Alternately, the cooling agent can be separate reactive chemicals, that when combined, undergo an endothermic reaction to provide a cooling affect. In one preferred embodiment, the cooling agent is substantially all water, with the addition of a small quantity of preservative. Water provides several operational advantages, including the ability to be frozen in a conventional freezer. Water is also low cost and benign when disposed of in an appropriate manner. Furthermore, it is typically non-staining in the event of a puncture or a rupture of the envelope 12, and furthermore, non-reactive with most other materials. Alternately, gels or other well known coolable materials can be employed as the cooling agent 24.

The bandage sheet 14 is positioned over the upper envelope layer 16 and extends longitudinally outward beyond the envelope outer perimeter 20 to define a pair of oppositely positioned mounting tabs 26. The bandage sheet 14 is formed of a flexible hypo-allergenic material for contact with skin. In one cold pack constructed in accordance with the invention, the bandage sheet 14 has been formed of a 3.7 mil polyethylene sheet.

The bandage sheet 14 defines an upper bandage surface 28 and an opposite lower bandage surface 30 oriented toward the envelope 12. A mounting adhesive 32 is positioned between the lower bandage surface 30 and the upper envelope layer 16. The mounting adhesive 32 permanently mounts the bandage sheet 14 to the envelope 12. The mounting adhesive 22 is sufficiently robust to undergo freezing and thawing while still maintaining the bandage sheet 14 in contact with the envelope 12.

The mounting tabs 26 are preferably sized such that they extend both longitudinally and transversely from the outer perimeter 20 of the envelope 12. In other words, the bandage sheet 14 defines an hourglass or dumbbell shape with envelope 12 at the central portion and the mounting tabs 26 on the outer portions of the bandage sheet 14. Therefore, the mounting tabs 26 have increased surface area for improved adhesive support of the cold pack 10 to the patient. The transverse extension of the mounting tabs 26 provides a larger mounting area of the mounting tabs 26 without an increase in the length of the self-adhering cold pack 10.

A bandage adhesive 34 forms a layer on the lower bandage surface 30 of the mounting tabs 26. The bandage adhesive 34 is a hypo-allergenic adhesive for temporary adhesion of the mounting tabs 26 to the skin surface of a patient. The bandage adhesive 34 can be one of many conventional hypo-allergenic adhesives conventionally employed for medical use. The mounting adhesive 32 and bandage adhesive 34 can be of different composition directed to the particular function of each adhesive 32, 34. However, the same hypo-allergenic adhesive is preferably employed for both adhesives 32, 34.

Base sheets 36 cover the bandage adhesive 34 on the mounting tabs 26. The base sheets 36 maintain the bandage adhesive 34 in operating condition until application of the self-adhering cold pack 10 to the patient. The base sheets 36 can be paper or other severable material that is readily releasable from the bandage adhesive 34. The base sheets 36 can be coated with wax or other compositions for improved release. The base sheets 36 can extend longitudinally or transversely beyond the outer edge of the mounting tabs 26 for simplified removal of the base sheets 36 from the mounting tabs 26.

In use, the self-adhering cold pack 10, having a cooling agent 24 of substantially all water, is supplied in an unfrozen state. The user can place the self-adhering cold pack 10 in a conventional freezer until the cooling agent 24 is completely solidified. In use, the self-adhering cold pack 10 will typically be affixed to the patient over a dressing or other padding. However, use of the self-adhering cold pack 10 is not limited to these circumstances. The self-adhering cold pack 10 is also intended for use on traumas that typically do not require a dressing, such as sprains or bruises. Self-adhering cold packs 10 having a large volume of cooling agent 24 are most appropriately used over a dressing. The dressing provides sufficient insulation for reducing the potential for excessive cooling of the skin of the patient. However, in some circumstances, the volume of the cooling agent 24 can be reduced whereby the cooling agent 24, in particular water, will reach room temperature prior to any potential over-cooling of the skin of the patient.

In one example of the self-adhering cold pack constructed in accordance with the invention for particular use in reducing swelling and patient discomfort after a breast biopsy, the envelope 12 defines a size of generally 2.5 inches in length and a width of approximately 1.25 inches. Approximately 12.5 ml of the cooling agent 24 is contained in the cold pack volume 22. The relatively reduced size of the self-adhering cold pack 10 allows positioning of the self-adhering cold pack 10 underneath clothing, yet still providing up to 20 minutes of cooling relief to the patient. In addition, this volume of the cooling agent 24 has been found to typically melt without the potential for excessive cooling to the patient even when in direct contact with the skin of a patient.

Figure 4:
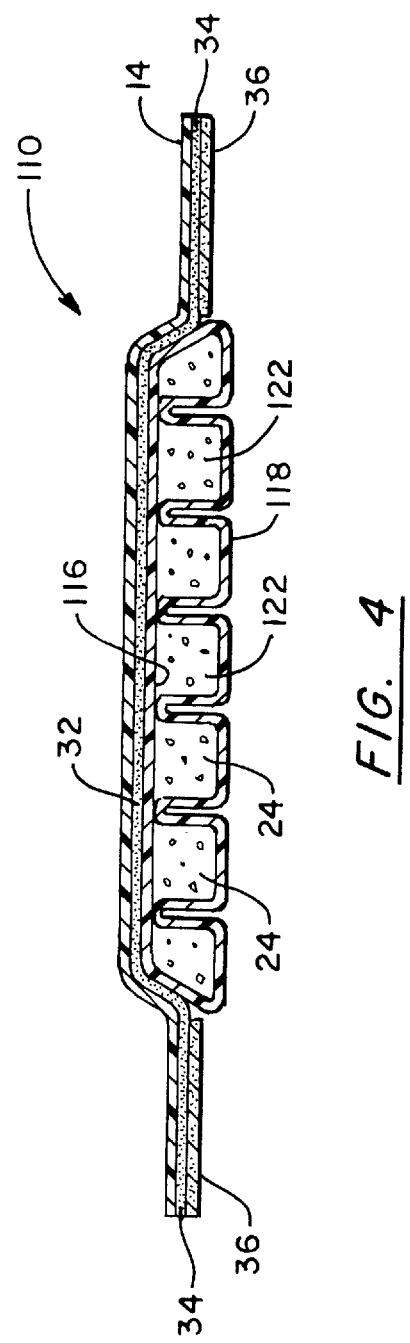
FIG. 4 is a cross-sectional view of the cold pack of FIG. 3 taken along the line 4—4.

In another embodiment of the invention, a self-adhering cold pack 110 has a multi-chamber envelope 112 defining a plurality of adjacent cells or chambers 122. (See FIGS. 3 and 4.) The multi-chamber envelope 112 has an upper envelope layer 116 and a lower envelope layer 118. The upper and lower envelope layers 112, 116 together define the plurality of chambers 122. Each chamber 122 is individually filled with the cooling agent 24. The adjacent chambers 122 provide the self-adhering cold pack 110 with increased flexibility. Therefore, the self-adhering cold pack 110 having the multi-chamber envelope 112 is particularly advantageous for use on contoured portions of the body. These contoured portions of the body include the nose whereby the self-adhering cold pack 110 can extend across the bridge of the nose, and the mounting tabs 26 are affixed to the upper cheeks of the patient.

Figure 5:
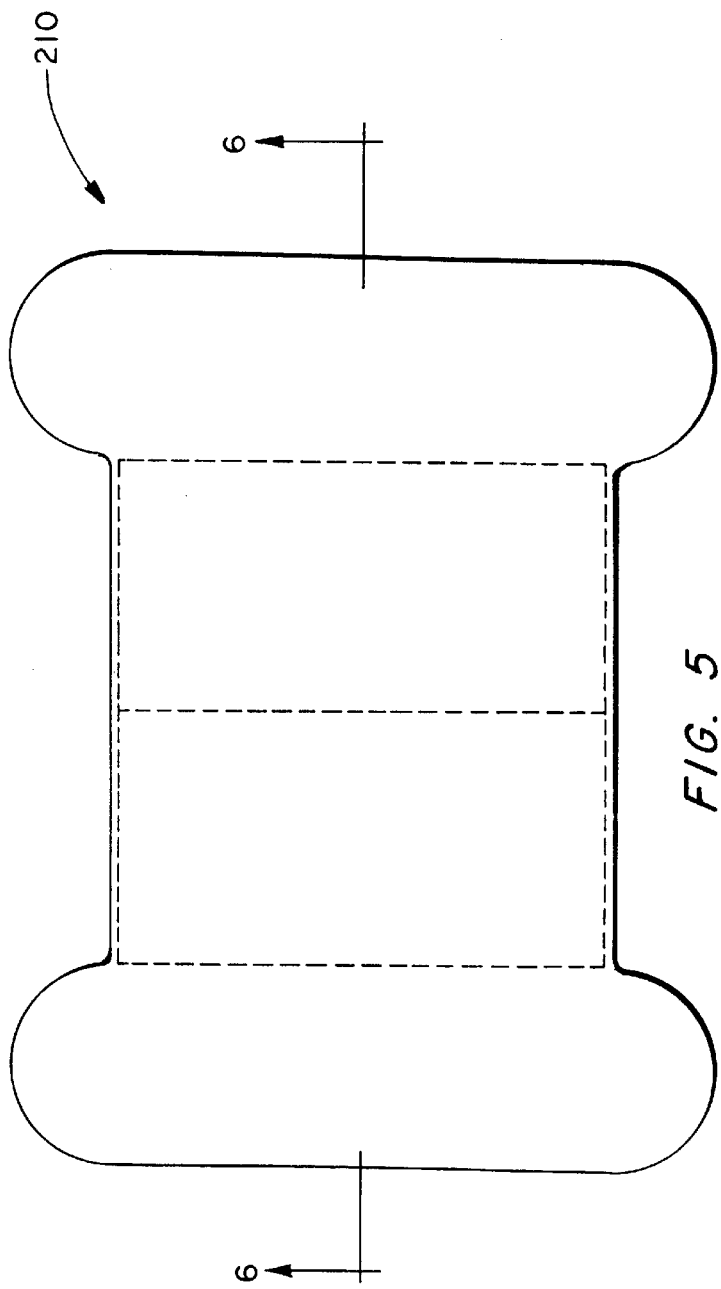
FIG. 5 is a top view, partially in phantom, of an alternate embodiment of the self-adhering cold pack of the invention.
Figure 6:
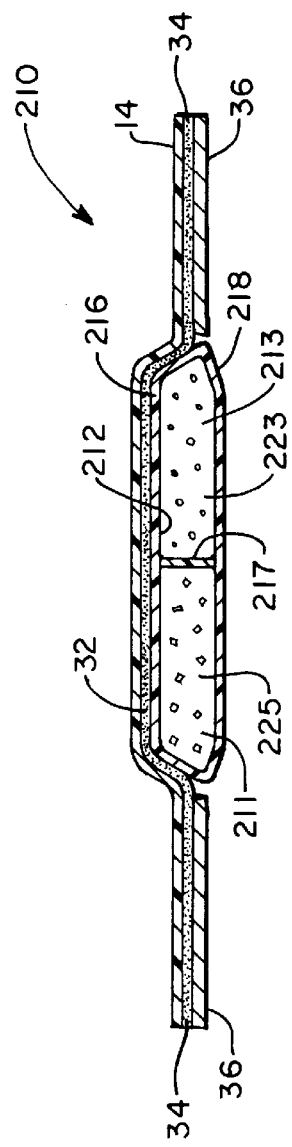
FIG. 6 is a cross-sectional view of the cold pack of FIG. 5 taken along the line 6—6.

In a further embodiment of the invention, a self-adhering cold pack 210 is self-cooling. (See FIGS. 5 and 6.) The self-adhering cold pack 210 has an internally rupturable envelope 212. The rupturable envelope 212 has an upper envelope layer 216 and a lower envelope layer 218 defining a cold pack volume 222. A divider wall 217 mounted between the upper and lower envelope layers 216, 218 divides the cold pack volume 222 into a sealed first chamber 211 and a separate sealed second chamber 213. The divider wall 217 is constructed to be readily more rupturable or breakable in comparison to the upper and lower envelope layers 216, 218. For example, partial perforations can be formed into the divider wall 217 to establish an area of reduced resistance to rupture. The cold pack volume 212 is provided with a cooling agent 24 comprised of a first reactive component 223 and a second reactive component 225 such that when the first and second reactive components 223, 225 are combined, they undergo an endothermic reaction to provide a cooling effect. The divider wall 217 maintains the first and second reactive components 223, 225 in the separate sealed first and second chambers 211, 213 until the self-adhering cold pack 210 is to be used. Squeezing or striking the internally rupturable envelope 212 breaks or ruptures the divider wall 217, allowing the first and second reactive components 223, 225 of the cooling agent 24 to mix and thereby undergo the endothermic reaction.

Examples of conventional first and second reactive components 223, 225 include water as a first reactive component 223 and either sodium nitrate or ammonium nitrate as the second reactive component 225. A self-cooling self-adhering cold pack constructed in accordance with the invention has an internally rupturable envelope 212 having dimensions generally of 3 inches by 4 inches, and first and second reactive agents 223, 225 of water and ammonium nitrate. This size of internal rupturable envelope 212 is sufficiently small to allow patient movement when the self-adhering cold pack 210 is used while still conferring a cooling effect for about twenty minutes.

Figure 7:
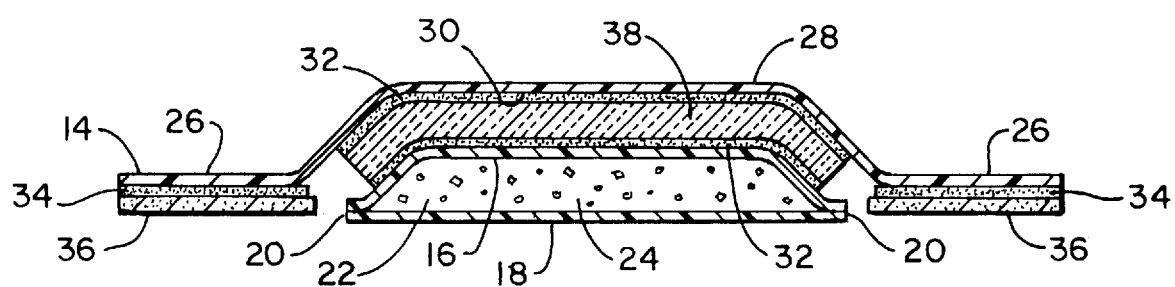
FIG. 7 is a cross-sectional view of an alternate embodiment of the cold pack of FIG. 1.

In a further embodiment, a self-adhering cold pack 310 has an extended cooling effect for the patient. An insulation layer 38 is positioned between the bandage 14 and the envelope 12 for extension of the cooling duration of the cooling agent 24. (See FIG. 7.) Mounting adhesive 32 is positioned between the lower surface 30 of the bandage 14 and the insulation layer, and also positioned between the upper envelope layer 16 and the insulation layer 38. The insulation layer 38 is preferably formed of a flexible foam material. The insulation layer 38 provides reduced heat gain through the bandage 14 thereby increasing the duration of the cooling effect to the skin of the patient.

While preferred embodiments of the present invention have been illustrated and described in detail, it should be readily appreciated that many modifications and changes thereto are within the ability of those of ordinary skill in the art. Therefore, the appended claims are intended to cover any and all of such modifications which fall within the true spirit and scope of the invention.

I claim:

1. A self-adhering cold pack comprising:

a liquid impermeable flexible envelope defining a closed internal cold pack volume and defining an outer perimeter edge;

a cooling agent in said cold pack volume;

a flexible bandage sheet engaging said envelope and having securement means extending longitudinally from said perimeter edge; and adhesive means for mounting said sheet to said envelope and for temporary adherence of said cold pack to a skin surface.

2. The self-adhering cold pack of claim 1 wherein said cooling agent comprises a water based solution.

3. The self-adhering cold pack of claim 1 wherein said cooling agent has a volume for said cooling agent reaching ambient temperature prior to over cooling of a skin surface.

4. The self-adhering cold pack of claim 1 wherein said envelope defines an envelope width and said tabs have a tab width greater than said envelope width.

5. The self-adhering cold pack of claim 1 further comprising a divider wall in said internal volume dividing said cold pack volume into first and second compartments and said cooling agent comprises a first component in said first compartment and a second component in said second compartment, said first and second components having an endothermic reaction when mixed.

6. The self-adhering cold pack of claim 5 wherein said divider wall is rupturable.

7. The self-adhering cold pack of claim 6 wherein said first component is water and said second component is ammonium nitrate.

8. The self-adhering cold pack of claim 1 wherein said bandage sheet has an upper surface and a lower surface, said adhesive means on said lower surface.

9. The self-adhering cold pack of claim 1 wherein said envelope forms a plurality of separate adjacent internal chambers.

10. The self-adhering cold pack of claim 1 further comprising an insulating layer between said bandage sheet and said envelope.

11. A self-adhering cold pack comprising:

a liquid impermeable envelope defining a closed internal cold pack volume and defining an outer perimeter edge;

a cooling agent comprising substantially water in said cold pack volume;

a flexible bandage sheet having a first surface and an opposite second surface, said second surface engaging said envelope and said sheet having securement tabs extending from said perimeter edge; and a hypo-allergenic adhesive on substantially all of said second surface for mounting said sheet to said envelope and for temporary adherence of said cold pack to a skin surface by said securement tabs.

12. The self-adhering cold pack of claim 11 wherein said envelope defines an envelope width and said tabs have a tab width greater than said envelope width.

13. The self-adhering cold pack of claim 11 wherein said envelope forms a plurality of adjacent internal chambers separated by said envelope.

14. The self-adhering cold pack of claim 11 further comprising adhesive cover sheets covering substantially the entire second surface of said tabs and mounted to said bandage sheet by said adhesive.

15. The self-adhering cold pack if claim 11 wherein said sheet is a polyethylene sheet.

16. The self-adhering cold pack of claim 11 wherein said cooling agent has a volume for said cooling agent reaching ambient temperature prior to over cooling of a skin surface.

17. The self-adhering cold pack of claim 11 further comprising an insulating layer between said bandage sheet and said envelope.

18. A self-adhering cold pack comprising:

a liquid impermeable envelope defining a closed internal cold pack volume and further defining an outer perimeter edge, said envelope having an upper envelope layer, a lower envelope layer, and a divider wall extending between said upper and lower envelope layers to divide said internal cold pack volume into a plurality of separate chambers, said divider wall rupturable;

a cooling agent in said cold pack volume comprising a first reactive component in one of said chambers, and a second reactive component in another of said chambers, said first and second reactive components having an endothermic reaction when mixed;

a flexible bandage sheet mounted to said envelope and having securement tabs extending from said perimeter edge; and a hypo-allergenic adhesive on said securement tabs for adherence of said cold pack to a skin surface.

19. The self-adhering cold pack of claim 18 wherein said first reactive component is water and said second reactive component is ammonium nitrate.

20. The self-adhering cold pack of claim 19 wherein said envelope has a dimension of about 3 inches by 4 inches.

* * * * *